United States Patent
Huber et al.

(10) Patent No.: US 9,683,896 B2
(45) Date of Patent: Jun. 20, 2017

(54) RAPID OPTICAL DELAY SCANNING METHOD AND APPARATUS USING TIME DEPENDENCE OF ACOUSTO-OPTIC DIFFRACTION

(71) Applicant: FASTLITE, Valbonne (FR)

(72) Inventors: Rupert Huber, Eilsbrun/Sinzin (DE); Olaf Schubert, Mintraching (DE); Daniel Kaplan, Paris (FR)

(73) Assignee: FASTLITE, Valbonne (FR)

( * ) Notice: Subject to any disclaimer, the term of this patent is extended or adjusted under 35 U.S.C. 154(b) by 158 days.

(21) Appl. No.: 14/377,582

(22) PCT Filed: Feb. 12, 2013

(86) PCT No.: PCT/EP2013/052748
§ 371 (c)(1),
(2) Date: Aug. 8, 2014

(87) PCT Pub. No.: WO2013/120832
PCT Pub. Date: Aug. 22, 2013

(65) Prior Publication Data
US 2015/0028214 A1    Jan. 29, 2015

(30) Foreign Application Priority Data

Feb. 14, 2012    (EP) .................................... 12155266

(51) Int. Cl.
*G01J 11/00*    (2006.01)
*G02F 1/11*    (2006.01)
(Continued)

(52) U.S. Cl.
CPC ................. *G01J 11/00* (2013.01); *G01J 5/10* (2013.01); *G02F 1/11* (2013.01); *G01N 21/3581* (2013.01);
(Continued)

(58) Field of Classification Search
CPC ........ G01J 11/00; G01J 5/10; G01N 21/3581; G01N 21/636; G01N 2201/0697; G02F 1/11; G02F 1/116; G02F 2203/13
(Continued)

(56) References Cited

U.S. PATENT DOCUMENTS 3,763,693 A * 10/1973 Bhuta ..................... G01N 29/06
                                                                348/163
5,778,016 A * 7/1998 Sucha ..................... G01P 3/806
                                                                372/38.1
6,072,813 A    6/2000 Tournois

FOREIGN PATENT DOCUMENTS

GB         2410081 A        7/2005

OTHER PUBLICATIONS

Maksimenka et al., "Direct mid-infrared femtosecond pulse shaping with a calomel acousto-optic programmable dispersive filter", Optics Letters, 2010, vol. 35, No. 21, pp. 3565-3567, XP001558189.

(Continued)

*Primary Examiner* — Marcus Taningco
(74) *Attorney, Agent, or Firm* — Young & Thompson

(57) ABSTRACT

A method and a system for scanning a time delay between a first ultrafast optical pulse of duration shorter than 10 ps and a second ultrafast optical pulse of duration shorter than 10 ps, wherein the second ultrafast pulse is submitted to an acousto-optic Bragg diffraction by an acoustic pulse in the bulk of an acousto-optic material and the delay scanning is produced by time variation of the acoustic pulse in the material.

17 Claims, 3 Drawing Sheets

(51) Int. Cl.
G01J 5/10 (2006.01)
G01N 21/3581 (2014.01)
G01N 21/63 (2006.01)

(52) U.S. Cl.
CPC ... *G01N 21/636* (2013.01); *G01N 2201/0697* (2013.01); *G02F 1/116* (2013.01); *G02F 2203/13* (2013.01); *G02F 2203/58* (2013.01)

(58) Field of Classification Search
USPC ........................................................ 250/340
See application file for complete search history.

(56) References Cited

OTHER PUBLICATIONS

Monmayrant et al., "A newcomers guide to ultrashort pulse shaping and characterization", Journal of Physics B: Atomic, Molecular and Optical Physics, 2010, vol. 43, pp. 1-34.

Piyaket et al., "Programmable ultrashort optical pulse delay using an acousto-optic deflector", Applied Optics, 1995, vol. 34, No. 8, pp. 1445-1453, XP000491228.

Riza, Nabeel A., "Acousto-optically switched optical delay lines", Optics Communications, 1998, vol. 145, pp. 15-20.

Topcu et al., "A new type of fiber-optic-based interferometric ellipsometer for in situ and real-time measurements", Review of Scientific Instruments, 2003, vol. 74, No. 10, pp. 4442-4447.

Verluise et al., "Arbitrary dispersion control of ultrashort optical pulses with acoustic waves", Journal of the Optical Society of America, 2000, vol. 17, No. 1, pp. 138-145, XP008048946.

International Search Report, dated May 7, 2013, from corresponding PCT application.

Bartels, A. et al.; "Ultrafast time-domain spectroscopy based on high-speed asynchronous optical sampling." Review of Scientific Instruments; vol. 78 (3): 2007; pp. 035107-1-035107-8, Konstanz, Germany.

Xu, Jieping, and Stroud, Robert; "Parametric Interaction and the Coupled-Wave Equation", Acousto-Optic Devices: Principles, Design, and Applications. Wiley-Interscience, Jun. 1992.

Kaplan, D. et al.; "Theory and performance of the acousto optic programmable dispersive filter used for femtosecond laser pulse shaping.", Journal de Physique IV Proceedings, vol. 12 (5): 69-75. 2002; (doi:10.1051/p4:20020098), pp. 1-7, Palaiseau, France.

Molchanov et al., "Acoustooptical delay lines for femtosecond pulse shaping based on crystal materials with strong acoustic anisotropy" Proceedings of SPIE—The International Society for Optical Engineering, vol. 7789, Oct. 2010, Bellingham, WA.

Chang, I. C., "Collinear beam acousto-optic tunable filters." Electronics Letters, vol. 28, No. 13, Jun. 18, 1992, pp. 1255-1256, Santa Clara, CA. doi:10.1049/el:19920793.

Voloshinov, Vitaly B. "Close to collinear acousto-optical interaction in paratellurite."; Optical Engineering, vol. 31, Issue 10, pp. 2089-2094, Oct. 1992, Moscow, Russia. doi:10.1117/12.58877.

Schenkel et al., "Generation of 3.8-fs pulses from adaptive compression of a cascaded hollow fiber supercontinuum."; Optics Letters, vol. 28, Issue 20, Oct. 15, 2003, pp. 1987-1989, Zurich, Switzerland. doi:10.1364/OL.28.001987.

* cited by examiner

RAPID OPTICAL DELAY SCANNING METHOD AND APPARATUS USING TIME DEPENDENCE OF ACOUSTO-OPTIC DIFFRACTION

BACKGROUND OF THE INVENTION

Field of the Invention

The availability of laser sources generating optical pulses of ultrashort duration (i.e. less than 10 picoseconds) has given the possibility to analyze the time dynamics of phenomena in specific media on time scales of picoseconds to attoseconds. These laser pulses are characterized by a broad spectrum of optical frequencies, the frequency range $\Delta v$ being related to the minimum duration of the pulse $\Delta t$ (also known as the Fourier Transform Limit) by the approximate relationship $\Delta v \approx 1/\Delta t$., implying $\Delta v$ values exceeding 0.1 TeraHertz (THz).

Description of the Related Art

A particularly effective method in the state of the art to achieve the study of time dynamics is the pump and probe technique, wherein an original laser pulse is used to produce two secondary pulses, named respectively pump pulse and probe pulse. The pump pulse excites the medium under study at time $t_0$, and the probe pulse suitably delayed by a time $\delta t$ with respect to the pump pulse is used to monitor some properties of the medium under study at time $t0+\delta t$. Repeating this experiments for different delay times $\delta t$ yields a kind of slow motion picture of the ultrafast dynamics. For instance, the probe pulse may traverse the medium and measuring its intensity can be used to monitor optical absorption as a function of time. An interesting variation of the pump and probe technique is Terahertz spectroscopy, wherein the pump pulse is sent to an electro-optic generator, to excite an electrical pulse in the THz range of frequencies. Examples of electro-optic generators are a photoconductor with an applied voltage or anon-linear optical material capable of optical rectification. An electro-optic detector is submitted to the probe pulse and to the THz wave, after it has interacted with the medium understudy. This achieves sampling of the THz wave. Such electro-optic detectors produce a signal proportional to the product of the THz wave electric field and the probe pulse energy. An implementation of an electro-optic detector can for instance use the polarization rotation in an electro-optic medium generated by the THz wave field, such rotation being measured by the transmission of the probe pulse through a suitable combination of the electro-optic medium and polarizers. A photoconductor polarized by the THz field and excited by the probe pulse can also be used as a detector.

In general, these measurements involve problems of sensitivity due to the small magnitude of the effects involved and to the short duration of the sampling probe pulse. It is usually necessary to sum the measurement observed over a number of successive laser pulses to obtain a meaningful result. Because measurements will always be subject to drifts of different origins, it is also desirable to vary rapidly the relevant parameter, in the present case the time delay, so that drifts can be minimal during the time of measurement. A desirable measurement condition, is thus to obtain a full measurement of the relevant delay interval in as short a time as possible, then repeat this measurement a sufficient number of times, summing separately the values for each individual $\delta t$, in order to improve the signal to noise ratio. From these considerations, it is clear that a scanning method for the delay $\delta t$ is required with the maximum possible repetition rate. Also, a high precision for the delay is desirable leading to criteria for the stability and the magnitude of the delay difference between successive optical pulses.

In the state of the art, two main scanning methods have been used. The first one uses a mechanical delay line, wherein the delay is controlled by the different in length of two separate optical paths, for the pump and probe pulse respectively. This method leads to notoriously low scanning rates, typically limited to a few tens of Hertz, due to the inertia of the mechanical components. It is thus inadequate for rapid scanning. Faster techniques have been developed based on rotatable mirrors or quickly moving loudspeaker diaphragms, which can attain scan rates of 100 Hz up to a few kHz. However, with a time jitter between scans far exceeding one femtosecond, these techniques are less precise and therefore unsuitable for analyzing processes occurring on few femtosecond and attosecond timescales. In a similar fashion, Piyaket et al. (Programmable ultrashort optical pulse delay using an acousto-optic deflector", Applied optics, Optical Society of America, Washington, D.C.; US vol. 34, no 8, 10 Mar. 1995, pages 1445-1453) have replaced the rotable mirror by an acousto-optic deflector, eliminating one source of timing jitter, but with remaining issues of mechanical stability and producing a delay scanning in discontinuous steps.

The second method, described for instance in "Bartels et al. 2007" (Bartels, A., R. Cerna, C. Kistner, A. Thoma, F. Hudert, C. Janke, and T. Dekorsy. 2007. "Ultrafast time-domain spectroscopy based on high-speed asynchronous optical sampling." Review of Scientific Instruments 78 (3): 035107), uses no mechanical delay, but instead relies on two separate laser sources for the pump and probe pulse respectively. These sources each generate a train of pulses, but the pulse repetition frequency is chosen to be slightly different for the pump and probe sources, by an amount $df=f_2-f_1$., where $f_2$ and $f_1$ are the probe and pulse repetition frequencies respectively. Hence for each successive pulse/probe pairs, the time difference between pulse and probe will be increased by a value $dt=1/f_1-1/f_2$. Using typical values of 100 MHz for $f_1$ and $f_2$ and $10^{-4}$ of relative difference $df/f$, it is possible to obtain 10000 different sampling points, by increments of 1 ps, in the scanning range of amplitude 0 to 10 ns, and a repetition rate of 10 KHz. The same reasoning applied to a 1 GHz repetition rate source yields a range of 1 ns and a repetition rate of 100 KHz. This method is generally referred as asynchronous optical sampling (ASOPS). Besides the complexity and cost associated with the requirement for two sources, the latter method has two disadvantages. First, many studies are interested in delay ranges significantly shorter than 1-10 ns. Consequently, a large part of the data measured is insignificant and lost. Second the synchronization between the two sources is done by electronic means and limited by inherent electronic jitter. The scan precision in the state of the art does not reach values below 50 fs. This is of the same order as the minimum difference of delay between successive pulses.

BRIEF SUMMARY OF THE INVENTION

It is the aim of the present invention to provide a scanning method, with rates of more than 1 kHz, scanning amplitude of order 10 ps and precision of 1 fs or better. The method is based on acousto-optic diffraction under Bragg conditions, denominated as Bragg diffraction, the principles of which are described for instance in "Xu and Stroud" (Xu, Jieping, and Robert Stroud. 1992. Acousto-Optic Devices: Principles, Design, and Applications. Wiley-Interscience, June.). The acousto-optic Bragg diffraction of ultrashort optical pulses, with broad frequency bandwidth, by multifrequency acoustic pulses has been described in the art, in particular in "Kaplan and Tournois 2002" (Kaplan, D., and P. Tournois. 2002. "Theory and performance of the acousto optic programmable dispersive filter used for femtosecond laser pulse shaping." Journal de Physique IV Proceedings 12 (5): 69-75. doi:10.1051/jp4:20020098). The present invention generates the time delay within the bulk of an acousto-optic crystal, as opposed to Piyaket et al. where an acousto-optic device is used as a mirror replacement to switch between several optical paths of different lengths in free space.

Considering first monochromatic optical and acoustic waves, it is known, that the diffraction of an optical wave by an acoustic wave satisfies the following phase conservation rule at any given point:

$$\phi = \phi_0 + \Phi + \text{constant} \quad (1)$$

where the respective phases $\phi$, $\phi_0$ and $\Phi$ of the diffracted wave, incident wave and acoustic wave are indicated. We consider a monochromatic acoustic real strain field of the form:

$$s = s_0 \cdot \text{Cos}(\vec{K} \cdot \vec{r} - \Omega T)$$

where $s_0$ is a constant, $\vec{r}$ is the position vector, $\vec{K}$ the acoustic wave vector, $\Omega$ the angular frequency associated with the acoustic wave and T the corresponding time, written as a capital letter. This field can be considered as the superposition of complex components proportional to Exp (i$\Phi$) and Exp(-i$\Phi$) where $$\Phi = \vec{K} \cdot \vec{r} - \Omega T$$

The theory of Bragg diffraction states that relation (1) has to be satisfied at all points in space for efficient diffraction, in a bulk medium, which leads to the wavevector conservation rule (Bragg law):

$$\vec{k} = \vec{k}_0 + \epsilon \cdot \vec{K}$$

where $\vec{k}$ and $\vec{k}_0$ are respectively the diffracted and incident optical wavector and $\epsilon$ is either +1 or -1 depending of which of the acoustic complex components has been used to satisfy the Bragg law. A frequency conservation rule is also necessary, but because acoustic frequencies are very small compared to the optical frequencies, it is appropriate to neglect the frequency change in the diffraction (Doppler effect) compared to the optical signal spectral bandwidth, and thus consider that the optical diffracted wave has the same angular frequency $\omega = 2\pi v$ as the incident wave.

Under conditions where Bragg law is satisfied, eq(1) implies the following relation.

$$\phi = \phi_0 + \epsilon \cdot \Omega \sim T + \text{constant} \quad (2)$$

For a given material, given geometric conditions and given optical frequencies, $\Omega$ is related to $\omega$. A person skilled in the art, taking into account the frequency dependence of optical indices of refraction, can derive from Bragg law the precise form relationship, which can be calculated with a high degree of precision. In the limit case, where the acoustic velocity does not depend on acoustic frequency and the optical indices of refraction do not depend on optical frequency, it is easily derived that $\Omega$ is proportional to $\omega$ with a proportionality factor K of order $10^{-7}$ to $10^{-5}$, depending on materials and geometric configurations. The people skilled in the art can then synthesize a multifrequency acoustic signal, with frequencies matching the frequencies present in the optical signal. This multifrequency acoustic signal will have the form of an acoustic pulse, whose time shape is the Fourier transform of its complex spectrum.

Derivating (2) with respect to optical angular frequency, one finds that the time delay $\tau$ of the diffracted optical wave is:

$$\tau = \frac{d\varphi}{d\omega} = \frac{d\varphi_0}{d\omega} + \varepsilon \cdot \frac{d\Omega}{d\omega} \cdot T \quad (3)$$

which demonstrates that the diffraction produces a time dependent delay, i.e. delay scanning. The sign of this scan is determined by $\epsilon$ and can be designed by the person skilled in the art to be positive or negative depending on the geometry used to satisfy Bragg law. The required function of scan delay is thus accomplished. If the differential of the acoustic frequency has a non negligible dependence upon frequency, i.e. if the factor K is not a constant, then the delay will be different for different spectral regions of the optical signal, i.e. the signal will be subject to some modifications of its time shape during the scanning process. This problem will be addressed in the final section of this description. For the time being, the relationship $\Omega = K \cdot \omega$ will be assumed, with the aim of simplifying the description of the invention principle.

In the art, the use of acoustic diffraction to control the spectral phase of an optical signal, by the phase of an acoustic signal using eq. (1), has been described in particular in "Kaplan and Tournois 2002", "Molchanov et al. 2010" Molchanov, V Ya, Sergey I Chizhikov, Oleg Y. Makarov, Efim A Khazanov, and Vladislav N Ginzburg. 2010. Acoustooptical delay lines for femtosecond pulse shaping based on crystal materials with strong acoustic anisotropy. In Vol. 7789. Proceedings of SPIE—The International Society for Optical Engineering. Bellingham, Wash., ETATS-UNIS: Society of Photo-Optical Instrumentation Engineers and "Pierre Tournois 2000" (Tournois, Pierre. 2000. Device for controlling light pulses by a programmable acoustooptic device. June 6) as a mean to achieve a given optical pulse time shape. In "Molchanov et al. 2010", the authors use the denomination "dispersive acousto-optic delay line" to describe the apparatus achieving this function. In App. No. EP0882251, the inventor addresses more specifically the use of this effect to control pulse compression in ultrafast amplifier system. In the three above references and similar references in the state of the art, the acoustic time variation between successive optical pulses is not considered, the acoustic shape being used to control the spectral phase within each pulse. None of these above references teaches the use of the acoustic signal time dependence to produce a time scan of the global delay of successive pulses subjected to the acousto-optic interaction (e.g. the probe pulses), compared to the delay of the same pulses not subjected to the acousto-optic interaction. (e.g. the pump pulses). The person trained in the art can secondarily adapt the phase of the acoustic signal at each frequency, to impart a given time shape to e.g. the probe pulse, but this is not claimed as an innovative feature of the present invention. In fact, within the scope of the present invention, the spectral phase dependence of e.g. the probe pulse upon the acoustic signal is a drawback mentioned in the previous paragraph and discussed in the final section of this description.

More specifically, if a train of pulses is generated with a time difference $\Delta T$ between each successive pulse, splitting each pulse into a pair of two replica and making one of them interact with the acoustic signal, will yield a time delay between the pair that will vary for each pulse instance. The delay characterizing the pair corresponding to the nth pulse in the train, will be given by $$\tau = n \cdot \epsilon K \cdot \Delta T + \text{constant} \qquad (4)$$

This accomplishes the goal of the invention to achieve delay scanning between successive pulses. For $K=10^{-7}$ and $\Delta T=10$ ns, $K \cdot \Delta T=0.1$ fs is significantly shorter than the 50 fs precision limit of ASOPS. Because of the compactness, it is possible to design short optical paths thus easing the requirement of stability of the optical path difference. The scan repetition rate is the inverse of the propagation time of typically 30 microseconds, i.e. of order 30 kHz.

A favorable condition for the operation of the invention will be one where the acoustic beam is collinear with the acoustic wave thus increasing the length of interaction. "Voloshinov 1992" (Voloshinov, Vitaly B. 1992. "Close to collinear acousto-optical interaction in paratellurite." Optical Engineering 31: 2089. doi:10.1117/12.58877) and "Chang 1992" Chang, I. C. 1992. "Collinear beam acousto-optic tunable filters." Electronics Letters 28 (13) (June 18): 1255-1256. doi:10.1049/e1:19920793 have taught how Bragg diffraction devices can be designed with collinear acoustic and optic propagation. The acousto-optic material used must be birefringent and acoustically anisotropic. The diffraction involves acoustic shear waves and the polarization of the input wave and the diffracted wave are at right angle. Examples of suitable materials for this purpose are Paratelllurite ($TeO_2$), Calomel ($Hg_2Cl_2$) and Lithium Niobate ($LiNbO_3$).

BRIEF DESCRIPTION OF THE DRAWINGS

The invention will be better understood, by considering the following example of realization.

DETAILED DESCRIPTION OF THE PREFERRED EMBODIMENTS

Figure 1:
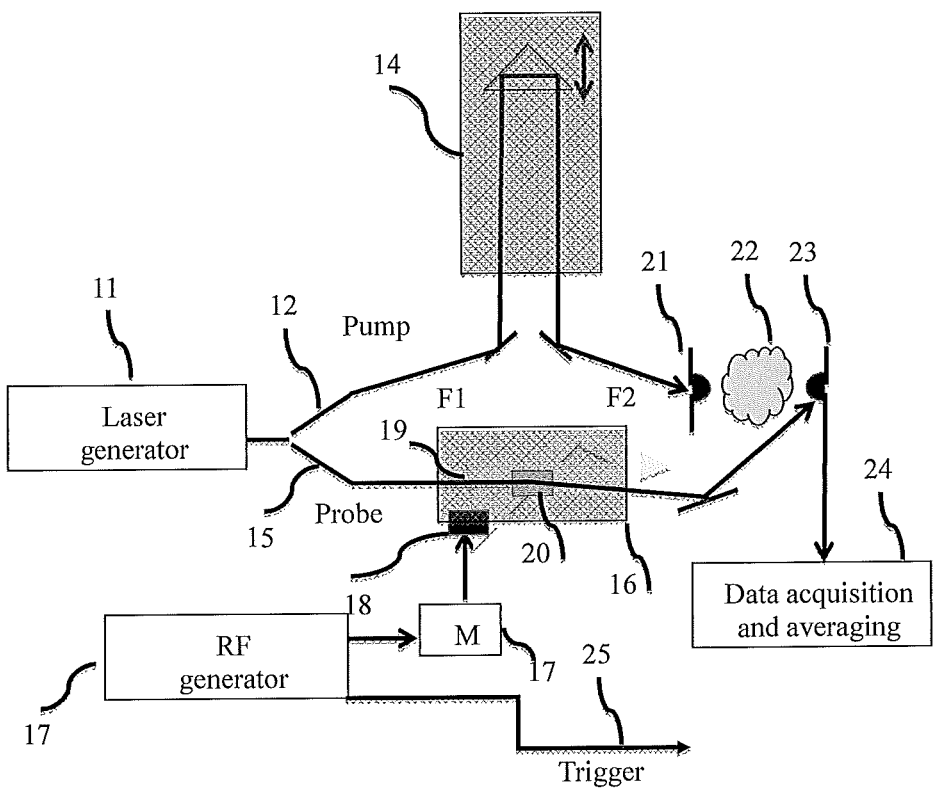
FIG. 1 illustrates a system for pump and probe studies according to the invention.

FIG. 1 presents an experimental arrangement whereby a laser pulse generator 11, delivers successive essentially identical laser pulses separated by $\Delta T$. Generator 11 may be an ultrafast laser oscillator delivering sub 100 fs duration pulses at a repetition frequency of order 100 MHz. The output of 11 is fed to an optical pulse splitter, which delivers two pulse replicas 12 and 15, to be used as pump and probe pulses respectively. In the example shown, rapid delay scanning will be performed on the probe pulse path 15, but it is clear that it can be accomplished equally well on the pump probe path. A collinear diffraction acousto-optic device 16, of the type discussed above is inserted in the probe optical path for the purpose of delay scanning. A mechanical delay line 14 is inserted in the pump pulse path to allow the experimenter to adjust the initial value of the time delay.

A Radio Frequency (RF) generator 17 is used to generate a signal containing acoustic frequencies matching the optical frequencies of the optical pulse for the purpose of acoustic diffraction. This signal takes the form of an RF pulse of duration Ta, which is fed to the transducer 18 of the acousto-optic device 16 by appropriate matching circuitry 17. The geometry of the device is chosen so that the acoustic path 19 involves the acoustic pulse first traveling to the optical input face F1, being reflected on F1, traveling to the optical output face F2, being reflected on F2, then being dissipated by some suitable arrangement. During the propagation time of duration Tp between F1 and F2, the acoustic pulse 20 can interact with the incoming successive probe pulses and produce diffracted pulses, whose delay will vary for every successive pulse, according to equation 4.

The diffracted output probe pulse is entered as a probe pulse into an experimental set up together with the input pump pulse. The example experimental set up shown as example is a THz experiment comprising a photoconductor as THz generator 21, driven by the pump pulse, a medium of THz interaction 22, a photoconductor 23 as THz detector submitted to the THz field and the probe pulse and a electronic data acquisition and averaging module 24 which receives the detector output and produces an average value as the detected signal as a function of delay. A trigger signal 25 produced by the RF generator 17 and received by the data acquisition module 24 is necessary to provide synchronization between scanning and acquisition.

Figure 2:
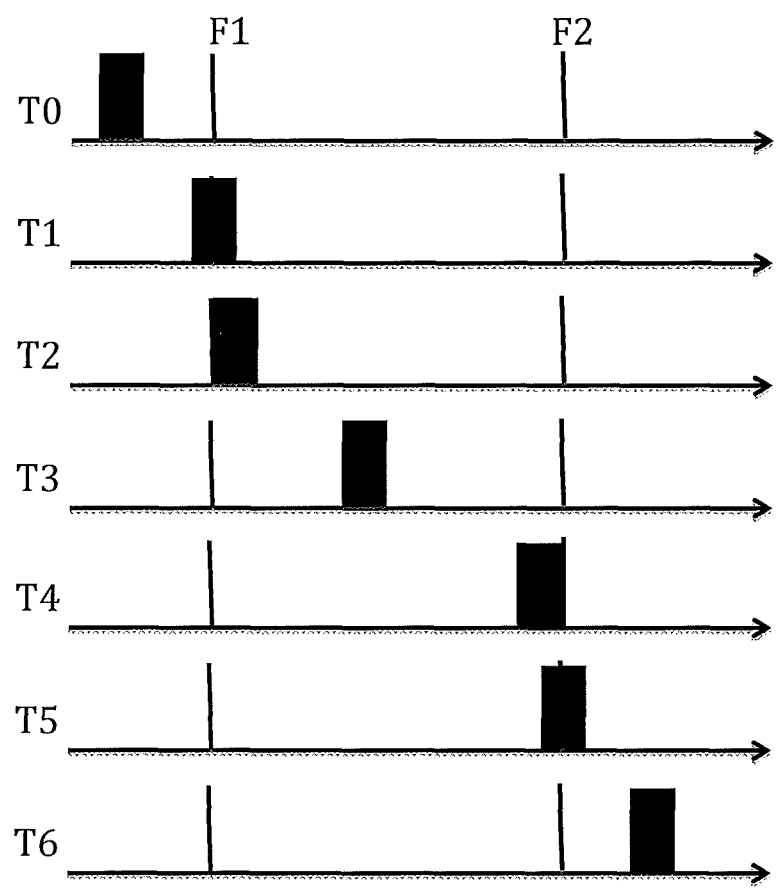
FIG. 2 illustrates a diagram of the acoustic pulse propagation in an acoustic optic device of the system of FIG. 1.

FIG. 2 shows a diagram of the acoustic pulse propagation in the device. At some initial time T0, the acoustic pulse in entirely out of the interaction zone F1-F2, between the optical faces. At time T1 it is has entered partially the zone. At time T2, it has entered completely the zone. At time T3 it is within the zone. At time T4, it reaches the end of the zone. At time T5, it is partially out the zone, and at time T6, it has completely left the zone. Clearly, the proper time zone of operation is between time T2 and T4. The duration of this time zone is Tp-Ta and the minimum repetition time is Tp in order to avoid the presence of two simultaneous signals in the interaction zone. There is thus a dead time of Ta. The experimenter will preferably take into account this dead time by suitable measures such as not acquiring signals during this period or not feeding the pump pulse during this dead time.

If the experiment does not allow for a dead time, a scheme must be provided to duplicate the interaction zone. For instance, two different optical paths, having each a separate acoustic device, with different synchronization conditions can be used, such that one device is in the proper T2-T4 zone of operation, while the other is in dead time conditions. Alternatively, a single device with multiple transducers and multiple corresponding acoustic paths, may be manufactured. Rapidly actively switching the probe signal, from one optical path to the next is a requirement. Ideally, this should be done in a time shorter than the separation between successive optical pulses.

Figure 3:
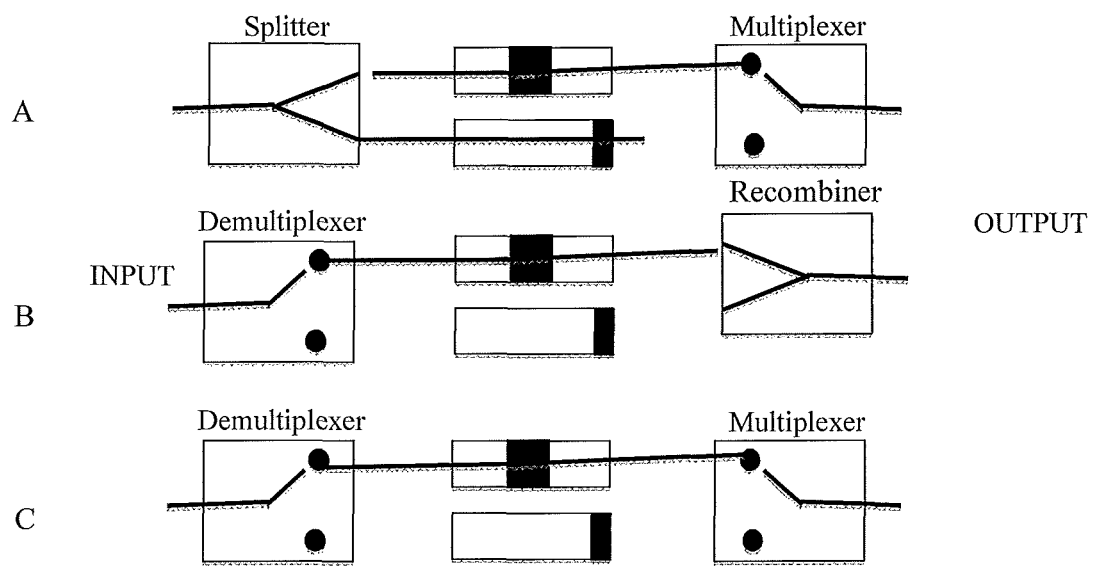
FIG. 3 illustrates that possible configurations (fig. a, fig. b, fig. c) to duplicate the interactions zone of a probe pulse.

FIG. 3 shows 3 possible configurations for achieving this. In FIG. 3 A the probe pulse is split into two replicas by a splitter. Each replica goes through a different path, each path being connected to a 2-1 multiplexer, i.e. a device allowing to switch rapidly from one to the other path at the appropriate instants. The switching control is accomplished by an electronic switching module, triggered by a proper digital signal output from the generator, which determines that for instance when the acoustic device in the bottom path of FIG. 3 A is in the dead time condition, the probe signal is received from the upper path which is in the proper zone of operation. Alternatively, FIG. 3B shows the probe pulse being sent to one or the other path by a demultiplexer, and the two paths being recombined by a recombiner. The two schemes above have the drawback of losing 50% of the energy with ideal components. FIG. 3 C shows a configuration where a demultiplexer is used at the entrance and multiplexer at the exit both being synchronized to the generator. Preferably these functions are implemented using guided optics technologies and fast electro-optic interactions are used for the switching functions.

Hereafter are described methods to operate under conditions of non-constant $$\frac{d\Omega}{d\omega}.$$

We now address the limitations introduced by the dependence on ω of $$\frac{d\Omega}{d\omega}.$$

This dependence is related to the dependence of the optical index parameters upon frequency and the corresponding changes in the wavevector conservation configuration. It is well known that for many materials there exists frequency domains where the index of refraction varies little with frequency. For instance, this is the case for Paratellurite in the vicinity of 3 micron wavelength. Experiments in this wavelength region, can use the invention even for broadband pulses.

Alternatively, in other wavelength regions, such as the vicinity of 0.8 micron where many ultrafast laser sources are operated, the condition for proper operation will be that the variation of delay over the total spectrum and for the full time range Tp, be significantly smaller that the intrinsic Fourier Transform Limit of the pulse duration for the total spectrum. It will then have a negligible effect on the experiment. Since the delay variation is proportional to the bandwidth and the Fourier Transform Limit inversely proportional to the bandwidth, the condition will be satisfied for small enough bandwidth. For operation in the vicinity of 800 nm, a bandwidth of 10 nm is a typical upper limit to satisfy the condition.

Figure 4:
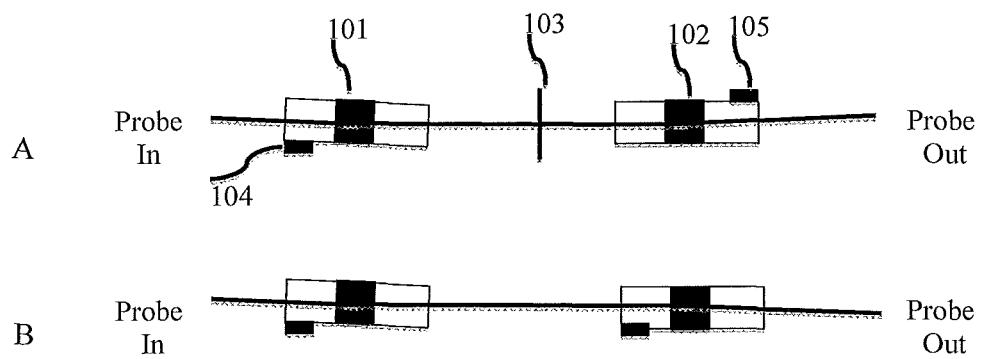
FIG. 4 illustrates two possible configurations (FIG. 4 A-FIG. t4B for a system to study electromagnetic properties of objects in the THz range of frequencies).

For larger bandwidths, a scheme such as the one shown in FIG. 4 can be used. In this figure the probe pulse is subject to two successive interactions, respectively in device 101 and device 102, or alternatively both pump and probe pulses are subjected to a single interaction. The device material and geometry will be chosen so that they compensate each other with respect to variations of the time shape. The essential condition is that the ratio $$\frac{\frac{d\Omega}{d\omega}}{\Omega}$$

be different from each other in the wavelength range of interest. If we use proper geometries, insuring that:
1: the factor ε is of opposite sign for both devices in eq 2,
2:

$$\frac{d\Omega}{d\omega}.$$

are equal for both devices.

The time broadening of both devices will cancel out, while the scanning effect will be $$\tau = (K_1 - K_2) \cdot T + \text{constant}$$

These conditions can for instance be satisfied using Paratellurite and Calomel for a wavelength near 1.5 micrometer.

FIG. 4 shows examples of configurations achieving this goal. In FIG. 4 A, devices 101 and 102 are both put on the probe pulse path. They diffract under identical conditions, but the transducers are put on opposite sides, so that the acoustic pulse travel in opposite directions. This yields factors of opposite signs. As the devices shown operate under collinear geometry, the polarization of the wave diffracted by device 101 is perpendicular to the input polarization, and device 103 (a waveplate) is used to restore the input polarization. In FIG. 4.B the input polarization is not restored and the diffraction in 102 restores the wavevector orientation and polarization of the input pulse. This also insures the reversal of sign of ε.

Another approach is in some cases possible. It is known in the state of the art that the bandwidth and duration of ultrafast optical pulses can be modified by non linear interaction. As an example, interaction in a rare gas is described in "Schenkel et al. 2003 (Schenkel, B., J. Biegert, U. Keller, C. Vozzi, M. Nisoli, G. Sansone, S. Stagira, S. De Silvestri, and O. Svelto. 2003. "Generation of 3.8-fs pulses from adaptive compression of a cascaded hollow fiber supercontinuum." Optics Letters 28 (20) (October 15): 1987-1989. doi:10.1364/OL.28.001987) and shown to increase the spectral bandwidth of a given pulse from tens of nanometers to hundreds of nanometers. The corresponding Fourier Transform Limit pulse duration will be reduced from the order of 100 fs to the order of 10 fs. A device performing this function will be labeled a broadener. The probe pulse is a narrow band pulse of bandwidth <10 nm, it is submitted to a scan delay in a device which does not modify its duration appreciably as discussed above. The output pulse is then fed into a broadener, e.g. a hollow core cylinder containing a rare earth gas. At the output of the cylinder, a short pulse is obtained which as negligible dependence upon the scanned delay. Preferably, an optical amplifier is added to the system, the probe pulse at the output of the broadener being fed into the amplifier to produce an output pulse with higher energy to compensate losses in acousto-optic diffraction and in the broadener. This scheme allows operation of the invention with short pulses of order 10 fs duration, for which the simple direct scheme of FIG. 1 would lead to very important modification of the pulse shape as a function of time delay.

The invention claimed is:
1. A method for scanning a time delay between successive first optical pulses of duration shorter than 10 ps and of a repetition rate larger than 1 MHz, and successive second optical pulses of duration shorter than 10 ps and of a repetition rate larger than 1 MHz, the method comprising:
   submitting the successive second optical pulses to a first acousto-optic Bragg diffraction by a single acoustic pulse traveling through the length of a bulk first acousto-optic material within a time T, a scan of the time delay being produced by a propagation of the acoustic pulse in said material during the time interval between the successive second pulses,
   wherein a full scan of the delay is obtained within the traveling time T.
2. The method according to claim 1, wherein the successive second optical pulses are submitted to a second acousto-optic diffraction in a second acousto-optic material, and wherein a time variation of pulse time shape by second acousto-optic diffraction compensates partially or totally a time variation of pulse time shape produced by the first acousto-optic diffraction.

3. The method according to claim 1, wherein the successive second optical pulses are secondarily submitted after said delay scanning to an optical non linear interaction yielding a pulse time shape essentially independent of the time variation of pulse time shape by the first acousto-optic diffraction.

4. The method according to claim 1, wherein a plurality of parallel optical paths of said successive second optical pulses are submitted to several acousto-optic diffractions by several acoustic pulses, each optical path interacting with a single acoustic pulses, the interaction having a finite interaction during T2, the acoustic pulses being identical but for their respective delays, the delays increasing with time with a delay increment smaller than T2 to reduce or eliminate dead time, the second optical pulses diffracted by each of the acoustic pulses being optically combined.

5. An apparatus for scanning a time delay between successive first and second ultrafast optical pulses of duration shorter than 10 ps having a same repetition rate that is larger than 1 MHz, the apparatus comprising:
a generator configured to generate an acoustic pulse containing acoustic frequencies matching optical frequencies of the optical pulses;
an acousto-optic material in which the successive second ultrafast optical pulses are submitted to an acousto-optic Bragg diffraction by the acoustic pulse in a bulk of the acousto-optic material, delay scanning being produced by a propagation of the acoustic pulse in the material during a time interval between successive second pulses, the acousto-optic material and an acousto-optic geometry being configured to achieve approximate collinearity between the optical beam propagation direction of said second optical pulses and an acoustic beam propagation direction of the acoustic pulse; and
a plurality of parallel optical paths of the second optical pulses having independent acousto-optic diffraction configurations, used sequentially in time to reduce or eliminate dead time.

6. The apparatus according to claim 5, further comprising a demultiplexer used to sequentially send pulses into said plurality of optical paths leading to interaction with said acoustic diffraction configurations.

7. The apparatus according to claim 6, further comprising an optical amplifier to amplify second optical pulse in order to compensate optical losses.

8. The apparatus according to claim 6, further comprising a broadener device configured to increase the pulse bandwidth after delay generation, the broadener achieving the bandwidth increase by non-linear interaction.

9. The apparatus according to claim 5, further comprising a multiplexer used to sequentially select pulses from said plurality of optical paths.

10. The apparatus according to claim 9, further comprising an optical amplifier to amplify second optical pulse in order to compensate optical losses.

11. The apparatus according to claim 9, further comprising a broadener device configured to increase the pulse bandwidth after delay generation, the broadener achieving the bandwidth increase by non-linear interaction.

12. The apparatus according to claim 5, further comprising an optical amplifier to amplify second optical pulse in order to compensate optical losses.

13. The apparatus according to claim 12, further comprising a broadener device configured to increase the pulse bandwidth after delay generation, the broadener achieving the bandwidth increase by non-linear interaction.

14. The apparatus according to claim 5, further comprising a broadener device configured to increase the pulse bandwidth after delay generation, the broadener achieving the bandwidth increase by non-linear interaction.

15. A system for pump and probe studies comprising:
the apparatus according to claim 5;
a laser generating a train of ultrafast light pulses;
a pulse splitter to separate each of said pulses into the first and second pulses, each of the pulses being one of a pump pulse and a probe pulse.

16. The system according to claim 15, wherein a mechanical pulse delay stage is added in the pump optical path or the probe optical path.

17. A system to study electromagnetic properties of objects in the THz range of frequencies using the system according to claim 15, wherein the pump pulse is used to generate a TeraHertz Wave using an electro-optic generation device, the TeraHertz being submitted to an interaction with the object of study producing a modified TeraHertz wave, the probe pulse being used to sample the modified TeraHertz wave at a given delay time using an electro-optic detector.

* * * * *